(12) United States Patent
Moonen et al.

(10) Patent No.: US 8,905,036 B2
(45) Date of Patent: Dec. 9, 2014

(54) ASSEMBLY FOR HEAT TREATMENT OF BIOLOGICAL TISSUES

(75) Inventors: Chrétien Moonen, Gradignan (FR); Bruno Quesson, Bordeaux (FR); Frédéric Vimeux, Blagnac (FR)

(73) Assignee: Koninklijke Philips N.V., Eindhoven (NL)

( * ) Notice: Subject to any disclaimer, the term of this patent is extended or adjusted under 35 U.S.C. 154(b) by 1196 days.

(21) Appl. No.: 12/829,097

(22) Filed: Jul. 1, 2010

(65) Prior Publication Data

US 2010/0268064 A1    Oct. 21, 2010

Related U.S. Application Data

(62) Division of application No. 10/475,108, filed as application No. PCT/FR02/01352 on Apr. 19, 2002, now abandoned.

(30) Foreign Application Priority Data

Apr. 20, 2001 (FR) .................................... 01 05410
Aug. 22, 2001 (FR) .................................... 01 10992

(51) Int. Cl.
*A61F 7/00* (2006.01)
*A61B 5/055* (2006.01)
*A61B 5/01* (2006.01)
*A61N 7/02* (2006.01)
*A61B 17/00* (2006.01)
*A61B 19/00* (2006.01)

(52) U.S. Cl.
CPC ......... *A61N 7/02* (2013.01); *A61B 2017/00084* (2013.01); *A61B 2019/5236* (2013.01)
USPC ............ 128/898; 607/96; 607/102; 600/411; 600/412; 600/549

(58) Field of Classification Search
CPC .................................... A61N 7/02; A61F 7/00
USPC ............ 607/96, 98–102; 600/400–412, 549, 600/552; 604/19, 22; 128/898
See application file for complete search history.

(56) References Cited

U.S. PATENT DOCUMENTS 5,368,031 A * 11/1994 Cline et al. .................... 600/411
5,485,839 A    1/1996 Aida et al.
5,620,479 A * 4/1997 Diederich ........................ 601/3
5,662,643 A    9/1997 Kung et al.

(Continued)

FOREIGN PATENT DOCUMENTS

EP    0 558 029    9/1993
FR    2 798 296    * 3/2001 ............... A61N 7/02

*Primary Examiner* — Ahmed Farah (57) ABSTRACT

The invention concerns an assembly for heat treatment of a region of a biological tissue (410) comprising energy-generating means (100) to supply energy to the region; means (200) for measuring and recording spatial temperature distribution in said region; a control unit (300) comprising means for point-to-point digital processing of the temperature distribution in the region. The invention is characterised in that the energy-generating means comprise means(110) for spatial and temporal distribution of the power available to them on said region, the control unit (300) comprising means (330, 350), based on the temperature distribution, for controlling the amount and distribution of energy supplied by the generating means (100).

11 Claims, 5 Drawing Sheets (56) References Cited

U.S. PATENT DOCUMENTS

| | | | |
|---|---|---|---|
| 6,128,522 A * | 10/2000 | Acker et al. | 600/411 |
| 6,788,977 B2 * | 9/2004 | Fenn et al. | 607/101 |
| 6,823,216 B1 * | 11/2004 | Salomir et al. | 607/101 |
| 6,939,344 B2 | 9/2005 | Kreindel | |
| 7,044,960 B2 | 5/2006 | Voorhees et al. | |
| 7,056,334 B2 | 6/2006 | Lennox | |

* cited by examiner

FIG_4

FIG_5

FIG_6

FIG_7

FIG_8

FIG_9

ASSEMBLY FOR HEAT TREATMENT OF BIOLOGICAL TISSUES

CROSS-REFERENCE TO RELATED APPLICATIONS

This application is a continuation of U.S. application Ser. No. 10/475,108, filed on Oct. 17, 2003, which is a national stage entry of PCT/FRO2/01352, filed on Apr. 19, 2002, which claims priority to French Application Serial No. FR 01/05410, filed on Apr. 20, 2001, each of which is incorporated by reference in its entirety.

STATEMENT REGARDING FEDERALLY SPONSORED RESEARCH OR DEVELOPMENT Not Applicable.

THE NAMES OF THE PARTIES TO A JOINT RESEARCH AGREEMENT Not Applicable.

INCORPORATION-BY-REFERENCE OF MATERIAL SUBMITTED ON A COMPACT DISC OR AS A TEXT FILE VIA THE OFFICE ELECTRONIC FILING SYSTEM (EF WEB) Not Applicable.

STATEMENT REGARDING PRIOR DISCLOSURES BY THE INVENTOR OR A JOINT INVENTOR Not Applicable.

BACKGROUND OF THE INVENTION (1) Field of the Invention

The invention relates to local hyperthermia therapies.

(2) Description of Related Art

Local hyperthermia therapies are techniques that are commonly used to locally treat biological tissues. They consist in heating a target zone of the biological tissue using an energy source (laser, microwave, radiofrequency wave, ultrasound, etc.).

These techniques offer numerous advantages. From the qualitative viewpoint, they offer a great deal of potential for controlling treatments such as gene therapy, the localized application of drugs, the ablation of tumours, etc. From an economic viewpoint, they are compatible with ambulatory treatment of the sick and therefore make it possible to reduce the hospitalization time.

In general, local hyperthermia therapies allow medical interventions the invasive nature of which is reduced to a minimum.

Among the types of energy used, focused ultrasound (FUS) is particularly advantageous because it is able to heat the focused-on zone, in a non-invasive way, deeply within the biological body, without significantly heating the tissues adjacent to the focused-on zone.

During treatment, the temperature of the target zone and of its immediate surroundings needs to be controlled precisely and continuously, although the supply of energy is localized and fast (of the order of a few seconds). U.S. Pat. No. FR 2 798 296 filed on Sep. 13, 1999 in the name of the *Centre National de la Recherche Scientifique* (CNRS) describes an assembly for the heat treatment of biological tissues. The assembly described in that document takes account of the actual spatial distribution of temperature in the target zone and in its immediate surroundings. This spatial distribution makes it possible to estimate precisely how much energy needs to be applied and to influence the energy source accordingly. Such an assembly makes it possible both quickly to obtain the desired temperature in the target zone and to maintain and control the temperature in this target zone with increased precision, by comparison with that which was possible with earlier techniques.

The disadvantage with this assembly is that it is based on a model of a heated region that is very localized in space. In consequence, it allows control over the change in temperature in the target zone but does not allow control over the temperature distribution when several energy sources are used or when the energy is applied simultaneously to several places, for example using an array of emitters.

BRIEF SUMMARY OF THE INVENTION

It is an object of the present invention to alleviate these disadvantages by proposing a heat treatment assembly that allows extended control of the temperature in a region of the living tissue and that can be applied without spatial limitation as regards the application of energy.

To this end, the invention proposes an assembly for the heat treatment of a region of biological tissue comprising:
  energy-generating means to supply energy to the region,
  means for measuring and recording the spatial temperature distribution in said region,
  control unit comprising numerical processing means for the point-by-point processing of the spatial temperature distribution in the region, characterized in that the energy-generating means comprise means for spatially and temporally distributing the power that they apply to the aforesaid region, the control unit comprising means for, on the basis of the temperature distribution, controlling the amount and distribution of the energy supplied by the generating means.

The means for spatially and temporally distributing the power applied consist, for example, of an ultrasound transducer whose movement in space is controlled. The heated region can therefore be broader than the initial distribution of the energy source.

The heat treatment assembly according to the present invention advantageously takes account of the spatial temperature distribution at each point in the region. Unlike the heat treatment assemblies of the prior art, this characteristic allows control over the distribution of energy throughout the treated region rather than simply of the energy applied at a focused-on point. It thus allows three dimensional and real-time control over the change in temperature in the treated biological tissue.

Advantageously, the control unit of the heat treatment assembly may comprise means for estimating the energy losses in the region of the tissue on the basis of an estimate of the thermal conductivity and of the spatial temperature distribution in the region and its surroundings. This allows the temperature distribution in the heat treated tissues to be changed more quickly toward a reference distribution.

In one embodiment of the invention, the control unit comprises processing means to take account of the thermal conductivity at each point in the region.

In particular, the control unit may comprise means for measuring the temperature at each point of a plurality of points sampling the region and at regular time intervals and to deduce therefrom an estimate of the change in temperature as a function of thermal conductivity from one point of the spatial sample to another.

According to this implementation, the image of the region of the biological tissue is broken down into voxels and each voxel is associated with a point in the region. The processing unit associates a thermal conductivity and a temperature with each point. This "point-by-point" breakdown advantageously allows the change in temperature to be controlled throughout the region of the biological tissue.

Advantageously, the energy-generating means may emit focused ultrasound. Focused ultrasound allows heat to be supplied to a localized zone, non-invasively, even if this zone is situated deep within the human body or the animal.

Advantageously, the means for measuring and recording the spatial temperature distribution comprise a Magnetic Resonance Imaging apparatus (MRI). MRI allows full and non-invasive mapping of the temperatures in the zone being treated, with good spatial resolution (of the order of 1 millimeter) and excellent precision (of the order of 1° C.). Furthermore, the data collected by MRI can easily be numerically processed.

In one implementation of the invention, the amplitude pw of the power to be supplied at a point $\vec{r}$ at an instant t+Δt is calculated using a relationship of the type:

$$pw = \frac{Tp(\vec{r}, t+\Delta t) - FT^{-1}(T*(\vec{k}, t)e^{-k^2 D\Delta t})}{FT^{-1}\left(\alpha \frac{1-e^{-k^2 D\Delta t}}{Dk^2} S*(\vec{k})\right)}$$

where Tp($\vec{r}$,t+Δt) is the reference temperature at that point at the moment t+Δt, $FT^{-1}$ is an inverse Fourier transform, T* ($\vec{k}$,t) is the Fourier transform of the temperature measured at the moment t, D is the heat diffusion coefficient for the tissue, α is the energy absorption coefficient for the tissue, S*($\vec{k}$) is the Fourier transform of the spatial distribution of the applied energy S($\vec{r}$).

In this way, at each moment, the energy to be applied is automatically controlled by the processing means so as to force the temperature to follow a predefined reference profile. This characteristic makes it possible to ensure optimum safety for the patient. In practice, what this amounts to is calculating the power pw to be applied between two successive temperature measurements obtained by MRI.

Of course, the energy-generating means for inducing hyperthermia in the region of the tissues being treated comprise energy sources of the ultrasound, laser, microwave or radiofrequency type.

BRIEF DESCRIPTION OF THE SEVERAL VIEWS OF THE DRAWINGS

Other features and advantages will become further apparent from the description which follows, which is purely illustrative and nonlimiting and is to be read with reference to the attached figures among which.

DETAILED DESCRIPTION OF THE INVENTION

One of the embodiments of the invention is described hereinbelow in detail. By way of example, this embodiment of the invention corresponds to a local hyperthermia treatment assembly using focused ultrasound (FUS) controlled by magnetic resonance imaging (MRI).

Figure 1:
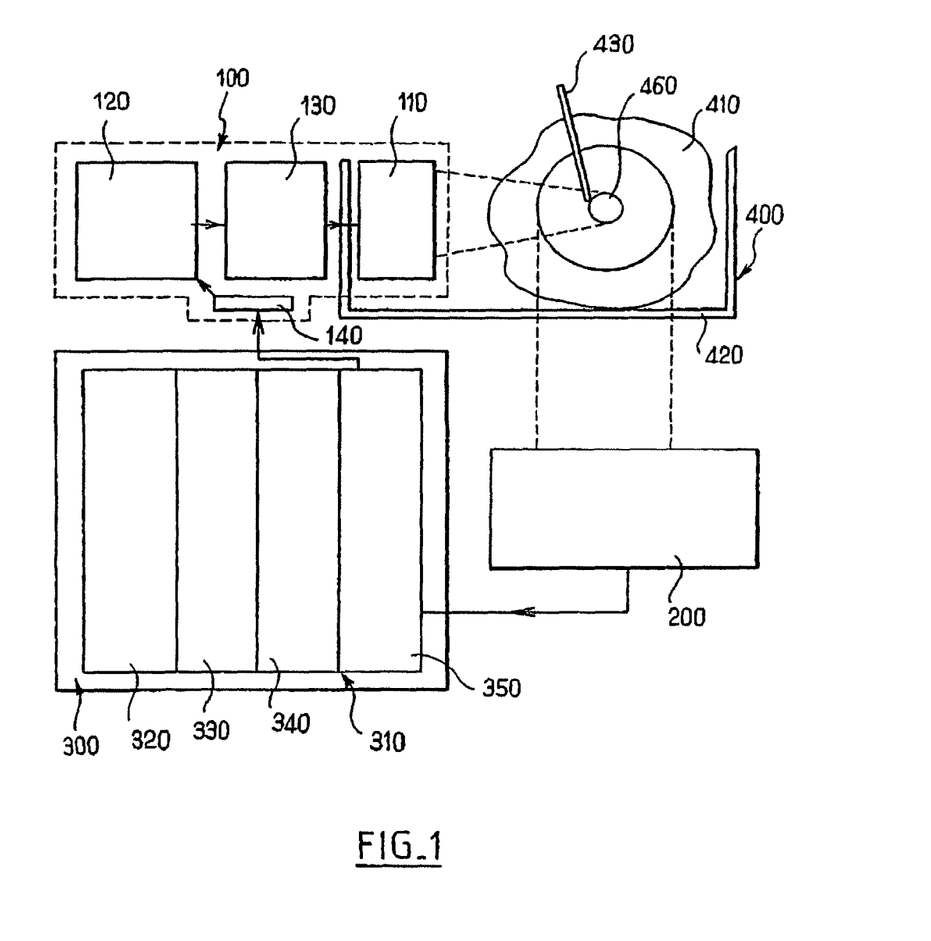
FIG. 1 schematically depicts the heat treatment assembly according to the invention.

As depicted in FIG. 1, such an assembly comprises:
ultrasound generating means 100,
anatomical and temperature mapping means 200,
a temperature control unit 300,
a sample holder 400 for the biological tissue 410 to be treated.

In the embodiment of the invention described here, the energy-generating means 100 are made up of a transducer 110 able to be moved by a hydraulic system, of a sinusoidal signal generator 120, of an amplifier 130 and of a converter 140 connecting the sinusoidal signal generator 120 to the control unit 300.

The transducer 110 has a diameter of 90 mm with a radius of curvature of 80 mm. The focal length can be adjusted electronically between 50 and 125 mm and the position of the focal region can be altered mechanically in the horizontal plane in a field of 80 mm×80 mm. It operates at 1.5 MHz. The input signal is generated by a multi-channel square wave generator. The signals are filtered so as to avoid interference with the magnetic resonance instruments that operate, for example, at 63 MHz for a 1.5T MRI apparatus.

The generator 120 is, for example, a multichannel generator (Corelec) driven by a serial connection. The system for moving the transducer in a horizontal plane is, for example, a hydraulic system driven by a serial link.

The aforesaid two links are connected, for example, to the PC receiving the MRI images in real time and producing temperature maps so as to allow the desired feedback control of temperature.

The mapping means 200 are able to measure and record the spatial temperature distribution. They comprise, for example, an MRI apparatus of the ACS NT 1.5 T type marketed by Philips® (Best, Netherlands). The control unit 300 in particular comprises a work station 310 of the PC type, marketed by Dell®. The PC is able to control the ultrasound generator 100 and the system for moving the transducer 110. In this device, all the parameters concerned with the application of energy by focused ultrasound can therefore be adjusted through the work station: the power of the ultrasound, the focal length and the position of the transducer 110. The work station further comprises a graphics interface so that the progress of the intervention can be viewed in real time.

The control unit 300 also comprises means for alleviating and numerically processing the spatial temperature distribution 320, means for determining the value of the power 330 that needs to be supplied to a target zone of the controlled region, means 340 for estimating thermal energy losses in the region considered and control means 350 for controlling the energy-generating means. The control means 350 tell the energy-generating means 100 to deliver the amount of power determined by the means for determining the power level 330.

The sample holder 400 comprises a support 420. This support contains the transducer 110 and a surface coil (MRI signal receiver). The support 420 is placed in a water-filled reservoir so as to ensure optimum propagation of the focused ultrasound toward the target tissues. The water is kept at a constant temperature of 38° C. using a water bath temperature controller (for example polysciences, model 9110-BB, IL, USA) to avoid the tested samples cooling.

The object of an automatic temperature control method is to force the temperature at a given position in the region of the samples for treatment to follow a reference profile Tp(t). The change in temperature in space and in time is given by the bio-heat equation [1] that takes account of the coefficient of energy absorption by the tissue ($\alpha$) and the coefficient of diffusion of heat into the tissue (D):

$$\frac{\partial T(\vec{r}, t)}{\partial t} = D \cdot \nabla^2 T(\vec{r}, t) + \alpha S(\vec{r}) \cdot pw(t) \qquad [1]$$

where $T(\vec{r}, t)$ is the temperature map, $\nabla^2$ is the Laplace operator, $S(\vec{r})$ is the spatial distribution of the applied energy and pw(t) is its amplitude.

This equation does not take account of perfusion in the tissues or of the heat produced by metabolism because the heat generated is neglible by comparison with the amount of heat applied by focused ultrasound (FUS). The invention generalizes the control principle based on equation 1 with no constraint regarding the spatial distribution of the application of energy by taking account of the heat transfer from each point (or voxel) to each other point (or voxel). To do that, an analytical solution for equation [1] is sought in order best to predict the temporal change in temperature at any point in space as a function of the diffusion and the application of energy by the source. The Fourier transform on the spatial coordinates of equation [1] leads to a linear equation of the first order as a function of time:

$$\frac{\partial T*(\vec{k}, t)}{\partial t} = -k^2 D T*(\vec{k}, t) + \alpha S*(\vec{k}) \cdot pw(t) \qquad [2]$$

where $T*(\vec{k},t)$ and $S*(\vec{k})$ are the Fourier transforms on the spatial coordinates of $T(\vec{r},t)$ and $S(\vec{r})$ respectively.

A solution can be derived from equation [2] by assuming the power pw(t) is constant for a given time interval $\Delta t$ (corresponding to the measurement interval for temperature measurements by MRI):

$$T*(\vec{k}, t+\Delta t) = e^{-k^2 D\Delta t} T*(\vec{k}, t) + \alpha \frac{1 - e^{-k^2 D\Delta t}}{Dk^2} S*(\vec{k}) \cdot pw \qquad [3]$$

In consequence, the power to be applied during $\Delta t$ to force the temperature $T(\vec{r}, t+\Delta t)$ to be equal to a temperature profile $Tp(\vec{r}, t+\Delta t)$ can be derived from the inverse Fourier transform (FT$^-$) of equation [3]:

$$pw = \frac{Tp(\vec{r}+\Delta t) - FT^{-1}(T*(\vec{k}, t)e^{-k^2 D\Delta t})}{FT^{-1}\left(\alpha \frac{1 - e^{-k^2 D\Delta t}}{Dk^2} S*(\vec{k})\right)} \qquad [4]$$

This type of algorithm makes it possible to ensure optimum safety for the patient because it makes it possible automatically to control the temperature. For this, the energy to be applied in order to force the temperature to follow a predefined reference profile is evaluated at regular time intervals $\Delta t$. In practice, what this amounts to is calculating the power pw to be applied between two successive temperature measurements obtained by MRI. Ideally, this type of algorithm takes the physical phenomenon (in this instance the heat diffusion equation) into consideration and is as robust as possible.

Setting up the Device

All the experiments were carried out according to the same protocol. The position of a reference volume was acquired in order to define a region of interest and the position of the reference focal point. The position of the reference volume with respect to the isocenter of the magnet of the MRI apparatus was recorded so as to position the transducer 110 and to adjust the focal length. Next, a repeated scan of this volume was done to prepare the heating process. This preparation was used to:

calculate the standard deviation at the temperature mean in each voxel of the volume so as to estimate the precision of the temperature measurement, correct the position of the transducer 110 and its focal length; low-power focused ultrasound was applied for a brief period (of the order of 5s) so as to induce modest hyperthermia (about +3° C.). This measurement made it possible to check the coordinates of the position of the image by magnetic resonance and the position of the transducer and the focal length were adjusted if necessary, evaluate the diffusion D and absorption a parameters of the tissue: focused ultrasound was applied for a brief period and a non-linear adjustment was made using the method of least squares to the curve of the change of temperature at the focal point as a function of time so as to obtain these parameters.

Following this preparatory protocol, the desired change in temperature as a function of time (reference profile $Tp(\vec{r},t)$) was programmed and the automatic control process (equation 4) was begun.

To allow this process to operate correctly, it was necessary to synchronize the MRI acquisition and the PC driving the focused ultrasound. For that, the MRI imaging device generates a TTL (Time to Live) signal at the start of each scan. This signal was detected by a built-in interface which switched a relay connected to a parallel port of the PC. This switching was detected by a special-purpose routine written in C and the corresponding PC system times were recorded in a shared memory module used by the algorithm. The timings thus measured were taken into consideration in the temperature control algorithm.

Experimental Procedure

Experiments on phantom gels, fresh meat samples and, in vivo on rabbit thighs, were carried out on the 1.5 Tesla Philips ACS/NT system equipped with the Philips prototype focused ultrasound generator for inducing local hyperthermia. Rabbits were anesthetized and positioned in such a way that the thigh muscles were centered approximately on the ultrasound beam. The values of the coefficients α and D from preliminary measurements are given in the table below:

|  | Acrylamide gel | Fresh meat | Rabbit thigh (in vivo) |
|---|---|---|---|
| $D(mm^2 \cdot s^{-1})$ | 0.17 | 0.36 | 0.10 |
| $\alpha(°C \cdot s^{-1} \cdot \%^{-1})$ | 0.33 | 0.29 | 0.40 |

When the preparatory adjustment phase had been carried out (see above), the real-time temperature control protocol was performed.

In these experiments, a temporal resolution of 1.75 seconds for 3 parallel slices was obtained, using a "segmented EPI" imaging technique with the following parameters: an echo time (TE) of 30 ms, a repeat time (TR) of 60 ms and 11 phase encoding steps per TR with a spatial resolution 1×1 mm, 3 mm slice thickness.

Figure 2:
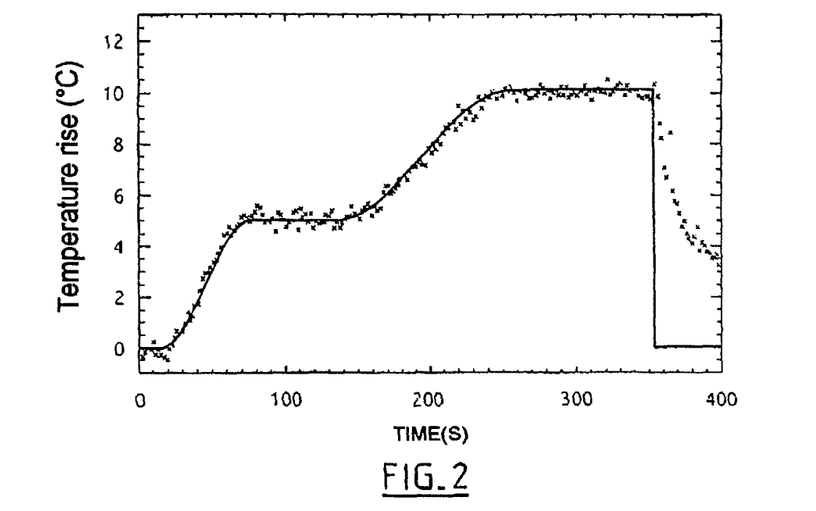
FIG. 2 depicts the change in temperature at the focal point of the transducer as a function of time when the method is applied to an acrylamide gel (test sample)
Figure 4:
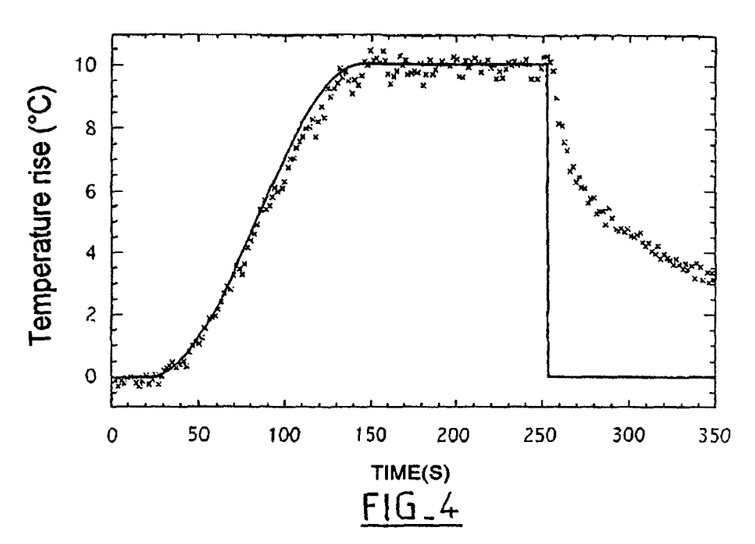
FIG. 4 depicts a change in temperature at the focus point of the transducer as a function of time when the method is applied to a fresh meat sample.
Figure 6:
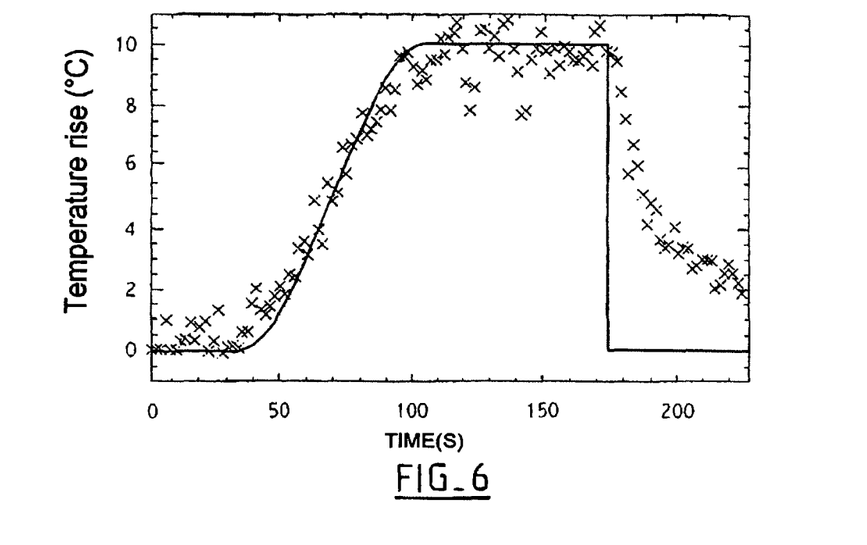
FIG. 6 represents the change in temperature at the focal point of the transducer as a function of time when the method is applied in vivo to the thigh of a rabbit.

FIGS. 2, 4 and 6 represent the change in temperature at the focal point of the focused ultrasound transducer as a function of time, obtained respectively with acrylamide gel, with a sample of fresh meat, and with a rabbit thigh. The curve in continuous line represents the reference temperature profile Tp(t) and the symbols represent the experimental temperature data at the focal point, measured by temperature MRI. As can be seen in FIG. 6, the application of focused ultrasound was halted after 170 s. The temperature then decreased to its initial value, with no control, on account of the diffusion phenomenon.

The standard deviation of the difference between the measured temperature and the reference temperature remained relatively constant (0.75° C. on average) during the hyperthermia phase, indicating that the proposed method makes it possible to perform effective real-time control on the change in temperature in vivo.

Figure 3:
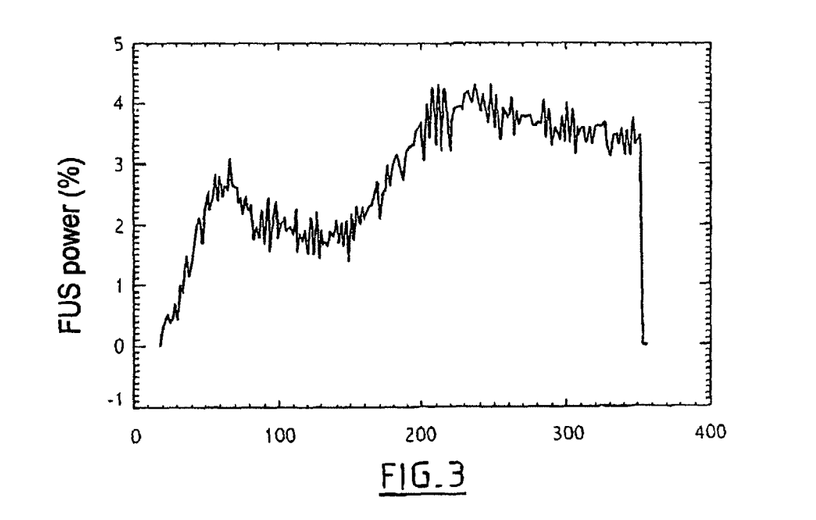
FIG. 3 depicts the change in power of the focused ultrasound as a function of time when the method is applied to an acrylamide gel.
Figure 5:
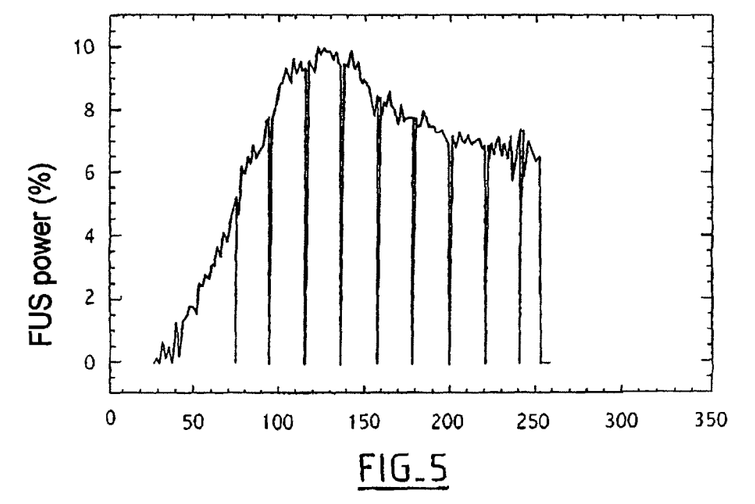
FIG. 5 depicts the change in power of the focused ultrasound as a function of time when the method is applied to a fresh meat sample.
Figure 7:
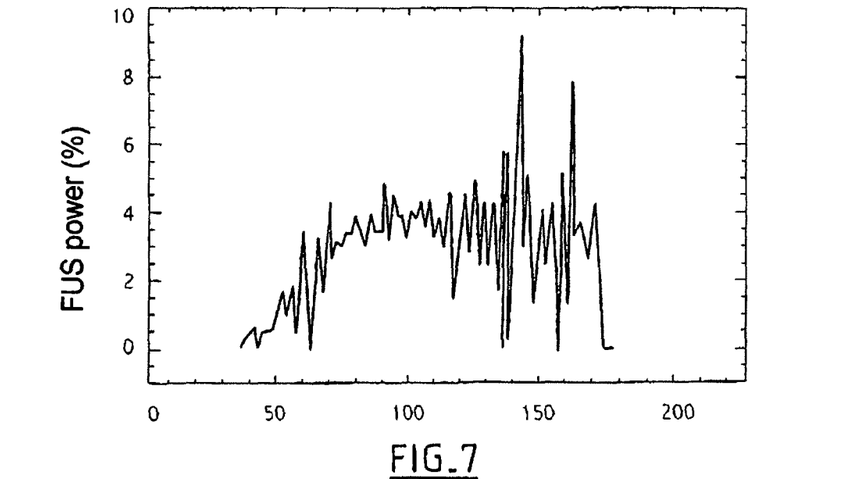
FIG. 7 depicts the change in power of the focused ultrasound as a function of time when the method is applied to the thigh of a rabbit.

FIGS. 3, 5 and 7 represent the change in focused ultrasound power as a function of time when the method is applied respectively to the acrylamide gel, to the fresh meat sample and to the rabbit thigh.

It is evident that the values of the coefficients a and D can vary during the experiment (as a function of temperature, because of the denaturing of proteins, change in perfusion, etc.). It is therefore important to make sure that the proposed temperature control algorithm is not excessively sensitive to a variation in these parameters.

The sensitivity of the quality of the temperature control was estimated from numerical simulations, by varying the parameters D and a over a wide range of values between 30% and 230% and between 50% and 150%, respectively, of their initially (on the basis of the preparatory phase) estimated value, in steps of 2%. For each (α, D) pairing, the change in temperature was calculated using the power actually applied during the experiment. The results obtained show that the temperature follows the temperature profile with an offset and with a fluctuation that vary to greater or lesser extents. The minimum difference between the simulated temperature and the reference temperature gives the offset value and the standard deviation of this difference allows the amplitude of the fluctuation to be evaluated.

Figure 8:
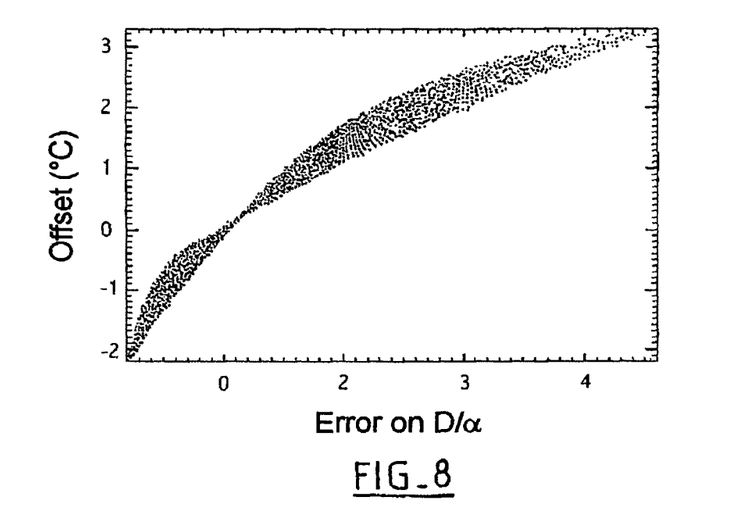
FIG. 8 depicts the variation in the minimum difference between the simulated temperature and the reference profile as a function of the error on the diffusion and absorption parameters of the treated tissues, which error is calculated as the ratio $$\frac{(D/\alpha) \text{ erroneous}}{(D/\alpha) \text{ optimum}}$$

FIG. 8 depicts the variation in the minimum difference between the simulated temperature and the reference profile as a function of the error on the diffusion and absorption parameters of the treated tissues, which error is calculated as the ratio $$\frac{(D/\alpha) \text{ erroneous}}{(D/\alpha) \text{ optimum}}$$

Figure 9:
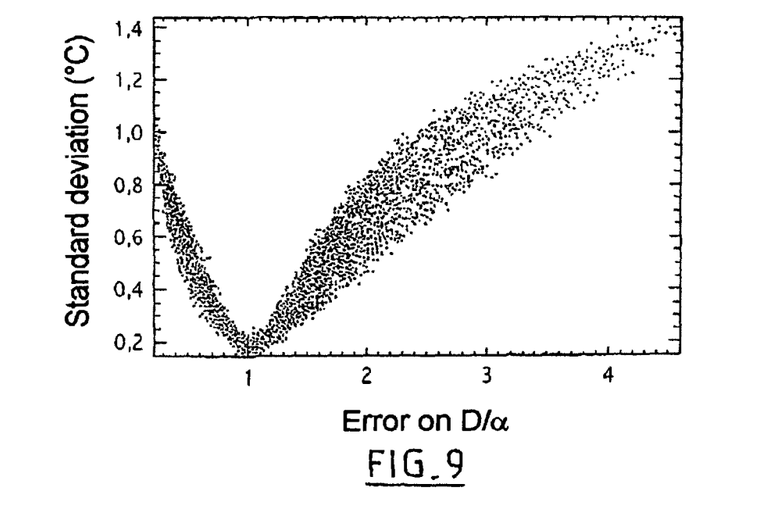
FIG. 9 depicts the variation in the standard deviation of the difference between the simulated temperature and the reference profile as a function of the error on the diffusion and absorption parameters of the treated tissues which error is calculated as the ratio $$\frac{(D/\alpha) \text{ erroneous}}{(D/\alpha) \text{ optimum}}.$$

FIG. 9 depicts the variation in the standard deviation of the difference between the simulated temperature and the reference profile as a function of the error on the diffusion and absorption parameters of the treated tissues, which error is calculated as the ratio $$\frac{(D/\alpha) \text{ erroneous}}{(D/\alpha) \text{ optimum}}.$$

These results reveal a significant correlation between the error in D/α and the precision of the control algorithm. In addition, it can be seen that an error in estimating a and D (due in particular to their variation during the course of the experiment) has little effect on the quality of the control. These results confirm the effectiveness and robustness of the proposed method.

The real time temperature control of local hyperthermia can be performed in vivo on a clinical MRI. This simple and predictive method based on the physical model of the temperature diffusion depends only on the absorption (α) and diffusion (D) coefficients of the tissues. The mathematical expression of the proposed algorithm is very general and can therefore be applied to any energy source (focused ultrasound, radiofrequency, laser, microwaves, etc.) that allows hyperthermia to be induced in biological tissues. The only condition governing its use is knowledge of the spatial profile of the application of energy.

The invention claimed is:

1. A method of heat treating a region of biological tissue comprising:
   supplying energy to the region including using a transducer for spatially and temporally distributing the energy applied to the aforesaid region;
   measuring and recording the spatial temperature distribution in said region using mapping means selected from an MRI or ultrasonic imaging device,
   point-by-point processing of the spatial temperature distribution in the region using a computer control station,
      wherein the computer control station controls the amount and distribution of energy supplied by the transducer to a target zone of a controlled region.

2. The method of claim 1, further comprising moving the transducer by a hydraulic system that is connected to the computer control station.

3. The method of claim 1, wherein the transducer is operably connected to a sinusoidal signal generator, an amplifier and a convertor.

4. The method of claim 3, wherein the convertor connects the sinusoidal signal generator to the computer control station.

5. The method of claim 1, further comprising estimating energy losses in the region of biological tissue on the basis of an estimate of the thermal conductivity and of the spatial temperature distribution in the region and its surroundings using the computer control station.

6. The method of claim 1, further taking into account the thermal conductivity at each point in the region.

7. The method of claim 6, further comprising
measuring the temperature at each point of a plurality of points, sampling the region and at regular time intervals and
deducing therefrom an estimate of the change in temperature as a function of thermal conductivity from one point of the spatial sample to another.

8. The method of claim 1, wherein the transducer is an ultrasonic transducer.

9. The method of claim 1, comprising calculating the amplitude pw of the power to be supplied at a point $\vec{r}$ at an instant t+Δt using a relationship of the type:

$$pw = \frac{Tp(\vec{r} + \Delta t) - FT^{-1}(T*(\vec{k}, t)e^{-k^2 D\Delta t})}{FT^{-1}\left(\alpha \frac{1 - e^{-k^2 D\Delta t}}{Dk^2} S*(\vec{k})\right)}$$

where Tp($\vec{r}$,t+Δt) is the reference temperature at that point at the moment t+Δt, $FT^{-1}$ is an inverse Fourier transform, T*($\vec{k}$,t) is the Fourier transform of the temperature measured at the moment t, D is the heat diffusion coefficient for the tissue, α is the energy absorption coefficient for the tissue, S*($\vec{k}$) the Fourier transform of the spatial distribution of the applied energy S($\vec{r}$).

10. The method of claim 1, wherein the transducer comprises energy sources of the ultrasound, laser, microwave or radiofrequency type.

11. A method for the heat treatment of a region of biological tissue comprising:

supplying energy to the region including using a transducer moved by a hydraulic system;

measuring and recording the spatial temperature distribution by using an MRI apparatus in said region, numerical processing for the point-by-point processing of the spatial temperature distribution in the region using a computer control station, wherein generating energy to the region comprises a transducer for spatially and temporally distributing the power applied to the aforesaid region, and the computer control station controls the amount and distribution of the energy supplied by the transducer, sinusoidal signal generator, amplifier, and convertor and further wherein the amplitude pw of the power to be supplied at a point $\vec{r}$ at an instant t+Δt is calculated using a relationship of the type:

$$pw = \frac{Tp(\vec{r} + \Delta t) - FT^{-1}(T*(\vec{k}, t)e^{-k^2 D\Delta t})}{FT^{-1}\left(\alpha \frac{1 - e^{-k^2 D\Delta t}}{Dk^2} S*(\vec{k})\right)}$$

where Tp($\vec{r}$,t+Δt) is the reference temperature at that point at the moment t+Δt, $FT^{-1}$ is an inverse Fourier transform, T*($\vec{k}$, t) is the Fourier transform of the temperature measured at the moment t, D is the heat diffusion coefficient for the tissue, α is the energy absorption coefficient for the tissue, S*($\vec{k}$) is the Fourier transform of the spatial distribution of the applied energy S($\vec{r}$).

* * * * *